US011299590B2

(12) United States Patent
Martinez et al.

(10) Patent No.: US 11,299,590 B2
(45) Date of Patent: Apr. 12, 2022

(54) PROCESS FOR PREPARATION OF BIOORGANIC NYLON POLYMERS AND THEIR USE AS ANTIBACTERIAL MATERIAL

(71) Applicants: Universite De Montpellier, Montpellier (FR); Centre National de la Recherche Scientifique (CNRS), Paris (FR)

(72) Inventors: Jean Martinez, Caux (FR); Ahmad Mehdi, Montpellier (FR); Gilles Subra, Saint Gely du Fesc (FR); Saïd Jebors, Jacou (FR)

(73) Assignees: Universite De Montpellier; Centre National de la Recherche Scientifique (CNRS)

( * ) Notice: Subject to any disclaimer, the term of this patent is extended or adjusted under 35 U.S.C. 154(b) by 16 days.

(21) Appl. No.: 16/060,751

(22) PCT Filed: Dec. 9, 2016

(86) PCT No.: PCT/EP2016/080517
§ 371 (c)(1),
(2) Date: Jun. 8, 2018

(87) PCT Pub. No.: WO2017/098018
PCT Pub. Date: Jun. 15, 2017

(65) Prior Publication Data
US 2019/0367670 A1    Dec. 5, 2019

(30) Foreign Application Priority Data
Dec. 9, 2015    (EP) ..................................... 15306964

(51) Int. Cl.
*C08G 69/36* (2006.01)
*C07K 17/08* (2006.01)
*C08G 69/10* (2006.01)

(52) U.S. Cl.
CPC .............. *C08G 69/36* (2013.01); *C07K 17/08* (2013.01); *C08G 69/10* (2013.01)

(58) Field of Classification Search
CPC .......... C07K 2/00; C07K 1/066; C08G 69/26; C08G 69/36
See application file for complete search history.

(56) References Cited

U.S. PATENT DOCUMENTS

| | | | |
|---|---|---|---|
| 6,517,933 B1 | 2/2003 | Soane et al. | |
| 7,709,601 B2 | 5/2010 | Cunningham et al. | |
| 2011/0152175 A1* | 6/2011 | Lipkowska | C07C 271/22 514/2.4 |

OTHER PUBLICATIONS

Jin et al (Synthesis of Polyamides and Polyureas Containing Leucine-Tyrosine Linkages, Journal of Polymer Sci, vol. 35, 499-507, (1997), published on Feb. 1997.*
Huang et al (Biodegradable Polymers Derived From Aminoacids, Macromol. Symp. 144, 7-32 (1999), published on Jun. 1999.*
Haralambidis et al (The preparation of polyamide-oligonucleotide probes containing multiple non-radioactive labels, Nucleic Acids Research, vol. 18, No. 3, published on Jun. 1990.*
Abdal-hay A, Hamdy AS, Morsi Y, Khalil KA, Lim JH. Novel bone regeneration matrix for next-generation biomaterial using a vertical array of carbonated hydroxyapatite nanoplates coated onto electrospun nylon 6 nanofibers. Materials Letters. Dec. 15, 2014;137:378-81.
Jia X, Herrera-Alonso M, McCarthy TJ. Nylon surface modification. Part 1. Targeting the amide groups for selective introduction of reactive functionalities. Polymer. Jun. 28, 2006;47(14):4916-24.
P. M. Mungara et al: "Synthesis of Functionalized Targeted Polyamides" In: "Polymers from Agricultural Coproducts",May 5, 1994 (May 5, 1994), American Chemical Society, Washington, DC, XP055273127, ISBN:978-0-8412-1496-5 vol. 575, pp. 160-170, DOI: 10.1021/bk-1994-0575.ch011, p. 162.
Nagata M, Kiyotsukuri T. Nylon-6 copolymers: copolymerization with a-amino acids. European polymer journal. Sep. 1, 1992;28(9):1069-72.
Kazuo Saotome, Rolf Schulz: "Optically Active Polyamides with Regular Structural Sequences Prepared from alpha-Amino Acid", Die Makromolekulare Chemie, vol. 109, Jun. 6, 1967 (Jun. 6, 1967), pp. 239-248, XP002757785, p. 240, last paragraph-p. 241, paragraph first.
Li Ngyun Wang et al: "Synthesis and Characterization of Novel Biodegradable Polyamides Containing [a 1 ph a]-ami no Acid". Journal of Macromolecular Science • Part A—Pure and Applied Chemistry., vol. 46, No. 3, Jan. 26, 2009 (Jan. 26, 2009). pp. 312-320, XP055272842. US ISSN: 1060-1325. DOI: 10.1080/10601320802637441.
International Search Report for PCT/EP2016/080517(published as WO2017098018) dated Mar. 30, 2017.
Jebors S, Ciccione J, Al-Halifa S, Nottelet B, Enjalbal C, M'Kadmi C, Amblard M, Mehdi A, Martinez J, Subra G. A New Way to Silicone-Based Peptide Polymers. Angewandte Chemie International Edition. Mar. 16, 2015;54(12):3778-82.

\* cited by examiner

*Primary Examiner* — Gregory Listvoyb
(74) *Attorney, Agent, or Firm* — Lerner, David, Littenberg, Krumholz & Mentlik, LLP

(57) ABSTRACT

The present invention relates to new biopolymer, i.e. bioorganic nylons incorporating peptidic blocks obtained by a process of polymerization of amino peptidic blocks. The process of the invention comprises the steps of mixing amino peptidic blocks with or without a diaminoalcane and reacting the mixture according to polycondensation with a diacyl chloride in homogeneous or heterogeneous media.

15 Claims, 3 Drawing Sheets
Specification includes a Sequence Listing.

PROCESS FOR PREPARATION OF BIOORGANIC NYLON POLYMERS AND THEIR USE AS ANTIBACTERIAL MATERIAL

The present invention relates to new biopolymers, i.e. bioorganic nylons incorporating peptidic blocks obtained by a process of polymerization of amino peptidic blocks. The amino peptidic blocks are mixed with or without a diamino-alcane and the mixture is reacted according to polycondensation with a diacyl chloride in homogeneous or heterogeneous media. The present process allows for a fine tuning of the ratio of peptidic blocks inserted in the final nylon type polymer thus permitting to control biological properties and activities of the bioorganic nylon thus obtained.

Nylons are a class of polymers widely used in everyday life and also in biomedical and day-to-day applications because they are tough, resistant and stable (A. Abdal-hay, A. Salam Hamdy, Y. Morsi, K. Abdelrazek Khalil, J. Hyun Lim, *Mater. Lett.* 2014, 137, 378-381). Moreover, they present an interesting hardness and good sliding properties, which are essential to realize efficient and removable stitches for example. For a variety of applications, however, it is necessary to impart desired properties by introducing specific functional groups in specific locations and densities. Several chemical modification methods were developed for the introduction of functional groups to nylon surfaces using amide-selective reactions without cleaving the polymer chains (Jia et al Polymer. Volume 47, Issue 14, 28 Jun. 2006, Pages 4916-4924).

Modification of nylons polymers are done after the polymerization and thus the fine control of the ratio, distribution, dispersion and quantity of the added functional groups, is not feasible.

For the particular case of biomaterials, the modification of nylons thanks to bioactive molecule appears to be a promising field of investigation.

U.S. Pat. No. 7,709,601 describes a process for selecting and identifying peptides with high affinity for nylon surface. In this case the functionalization thanks to bioactive peptides is achieved after the polymerization of the nylon and the bioactive peptides are only adsorbed on the surface.

Wang et al describe a process for the introduction of simple and mere amino acids into nylon scaffold structure, but not peptides. The described process includes the synthesis of a dimer of amino acid linked through a sebacoyl diacid which is activated as diacylchloride which is thus reacted through interfacial polycondensation with 1,6-hexanediamine (Synthesis and Characterization of Novel Biodegradable Polyamides Containing α-amino Acid Journal of Macromolecular Science, Part A: Pure and Applied Chemistry; Vol 46 (3); 2009; p 312-320).

Nagata et al describe the copolymerization of acid 6-amino-n-hexanoique with alanine, leucine, phenylalanine lysine for improving biodegradability of the thus obtained nylon (Nylon-6 copolymers: Copolymerization with α-amino acids European Polymer Journal; Vol 28 (9); 1992; p. 1069-1072). The obtained nylon is composed of two blocks which each possesses one amine function and one acid function.

These technologies are more directed to improve the biodegradability of the nylon, than to confer advantageous biological properties to the nylon and allow the introduction of single amino acid and not of peptide into a nylon type structure.

U.S. Pat. No. 6,517,933 describes hybrid polymer material or system that combines naturally occurring building blocks with synthetic building blocks. The sets of naturally occurring and synthetic building blocks are mixed and joined on a molecular or nanoscopic level to give homogeneous or microphase-separated morphologies to the resulting mixed polymer system. These hybrid polymers combine the comfort attributes of natural materials with the robustness and design properties of synthetic materials.

This document describes generic polymer structures incorporating natural building blocks however it does not disclose how a specific natural bioactive peptide can be integrated into a nylon type polymer neither does it describe how the ratio of integration can be controlled.

There is therefore a need for a process that allows the precise and controlled integration of bioactive residues, particularly peptidic residues, in a nylon polymer.

Accordingly, the present invention discloses a process for the preparation of bioorganic nylon type polymer comprising the steps of:

i) preparing a basic solution containing at least one type of peptidic amino-building block selected in the group consisting of the following A, B, C, D and E blocks:

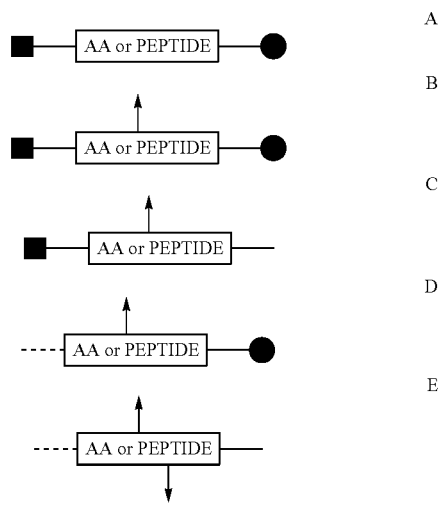

wherein:

AA is an amino-acid residue, PEPTIDE is a peptide residue;

■ is the $N_{terminus}$ of AA or PEPTIDE;

● is the amino derivatized $C_{terminus}$ of AA or PEPTIDE;

▲ is the free amino group of the side chain of AA or of an amino-acid residue of PEPTIDE;

─── is the $C_{terminus}$ of AA or PEPTIDE;

--- is the protected N terminus of the AA or PEPTIDE ii) polymerization by contacting the solution of i) with a solution containing a diacyl G of the following formula (G): X(CO)—Y—(CO)X wherein:

X is a halogen, preferably Cl

Y is $(CH_2)_q$, $C_6H_4$, $C_6H_4$—W—$C_6H_4$, $C_6F_4$, $C_6F_4$—W—$C_6F_4$, $C_{10}H_6$, q is comprised between 1 and 12, and W is a bond, $CH_2$, O, S, or $SiO_2[(CH_2)_rCH_3]_2$, with r comprised between 1 and 4, preferably r is 1.

As used herein, a $C_{10}H_6$, represents a naphthyl group of formula

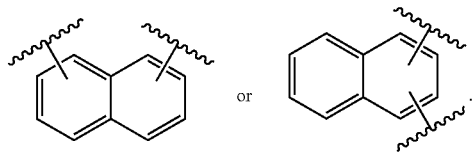

Preferably Y is $(CH_2)_q$ or $C_6H_4$ with q comprised between 1 and 12. In one embodiment Y is $(CH_2)_q$, wherein q is comprised between 1 and 12, particularly between 1 and 8, more particularly between 1 and 6. For instance, q is 4 or 8.

In an embodiment, the solution prepared in i) does contain two types of peptidic amino building blocks selected in the group consisting of A, B, C, D and E blocks.

In an embodiment, the solution prepared in i) does contain three types of peptidic amino building blocks selected in the group consisting of A, B, C, D and E blocks.

In an embodiment, the solution prepared in i) does contain four types of peptidic amino building blocks selected in the group consisting of A, B, C, D and E blocks.

In an embodiment, the solution prepared in i) does contain five types of peptidic amino building blocks selected in the group consisting of A, B, C, D and E blocks.

In another embodiment of the present invention, the solution of i) further contains a diamino building block F selected in the group consisting of diamino-alcane building block of general formula (F): $H_2N-Z-NH_2$ wherein Z is $(CH_2)$ p, $C_6H_4$, $C_6H_4-W'-C_6H_4$, $C_6F_4$, $C_6F_4-W'-C_6F_4$, $C_{10}H_6$, p is comprised between 1 and 14, W' is a bond, $CH_2$, O, S, or $SiO_2[(CH_2)_sCH_3]_2$ with s comprised between 1 and 4, preferably s is 1.

Preferably Z is $(CH_2)$ p or $C_6H_4$, with p comprised between 1 and 14. In one embodiment Z is $(CH_2)$ p, and p is comprised between 1 and 14, particularly between 1 and 8, more particularly between 1 and 6. For instance, p is 4 or 8.

The molar quantity of the different peptidic amino building blocks and diaminoalcane building block is such that it equals the molar quantity of DIACYL compound G: $[A+B+C+D+E]+[F]=[G]$.

Indeed [F] can vary from 0 to 99 and [A+B+C+D+E] can vary from 1 to 100 assuming that [G] equals 100.

The molar quantity of the various building blocks A, B, C, D or E may each vary from 0 to 100% of the total of [A+B+C+D+E]. Therefore, any combination of various types of peptidic amino building blocks can be used. One can then use only type A blocks, or only type B blocks, or only type C blocks, or only type D blocks or only type E blocks or any combination thereof.

Furthermore any combination of one, two, three, four or five peptidic amino building blocks is possible, assuming that molar quantity of the different peptidic amino building blocks, including the optional diamino alcane block, is such that it equals the molar quantity of DIACYL compound G as exposed above.

In a preferred embodiment the diacyl compound G is a diacyl chloride, more particularly adipoyl dichloride.

In one embodiment, the polymerization can be achieved in homogeneous or heterogeneous phase.

In the case the polymerization is achieved in homogeneous phase, the buildings blocks A to F are dissolved in a solvent which is also a solvent of the diacyl compound G.

Available solvents that are compatible with both building blocks A to F and diacyl compounds G can be selected in the group consisting of DMF, DMSO and dichloromethane for example.

In such a case, the obtained polymer is formed instantaneously in the media upon mixture of the two solutions and recovered by filtration for example. The thus formed recovered polymer can then be washed by aqueous or organic solvents.

When the polymerization is achieved in homogeneous phase, the alkalinity of the medium is ensured, thanks to the addition in the medium of a base which is miscible with the solvents used in the homogeneous polymerization. Suitable base can be di-isopropylethylamine (DIEA) for example.

In a further embodiment the polymerization is achieved in a heterogeneous phase, and initiated through interfacial polymerization. Interfacial polymerization techniques are well known techniques to the skilled person.

In such an embodiment, the building blocks A to F are solubilized in a basic aqueous solution and said solution is contacted with an organic solvent containing the diacyl compound G. Upon contact of both solutions, the polymerization occurs at the interface between both non-miscible liquids.

The nylon type polymer can thus be recovered from the interface by pulling it out progressively thus creating a new interface between the two phases wherein new polymerization occurs and new polymer is formed continuously.

The recovered polymer can then be washed. The washing can be achieved thanks to solvent such as water or any suitable organic solvent.

In the present invention, the expression basic solution of i) is to be understood as a medium whose pH is above 7, particularly above 8, more particularly above 9, even more particularly above 10 and even more particularly above 11.

In the embodiment of heterogeneous polymerization through interfacial polymerization, the diacyl compound G can be dissolved in an organic solvent which can be selected in the group consisting of dichloromethane, trichloroethylene and their mixtures for example.

Polymerization can be initiated at the interface between the basic aqueous solution containing the diamino building blocks, and the organic solvent phase, particularly the dichloromethane phase, which contains the diacyl compound G, particularly the diacyl chloride. The amine functions of the diamino building blocks A to F react with acid chloride, forming a polymer film at the interface.

Several types of peptide-nylons can be prepared this way. First, the percentage of peptidic blocks as well as of alcane blocks in the nylon can be simply tuned by choosing the ratio peptidic-diamino building blocks/diamino-alcane building blocks.

Accordingly, in a further embodiment, the present invention relates to a process wherein the molar concentration of peptidic-diamino building blocks [A+B+C+D+E] varies from 1 to 100% and the molar concentration of diaminoalcane building block [F] is comprised between 0 and 99%, the sum of both molar quantities being equal to 100% and corresponding to the molar quantity of diacyl compound [G] expressed as 100%.

According to the process of the invention and thanks to the choice of the aminopeptidic building blocks, the orientation of the peptide within the polymer chain can be chosen. When the C-terminus of the peptide is derivatized with a diamine, the peptide sequence is incorporated linearly in the chain of the polymer. In such a situation, if the AA or the PEPTIDE contains one or more side chains displaying a free primary or secondary amino group capable to engage in the polymerization reaction, said free amino group is protected thanks to a protecting group in order to prevent its engagement in the polymerization at step ii).

The polymers obtainable according to the process of the invention are characterized by the fact that at least one peptide motif is fully integrated within the polymeric chain and the content, the distribution of such peptide motif can be finely tuned thanks to the ratio of diamino peptidic blocks and diaminoalcane blocks. The thus obtained polymers, contrary to the nylon-type polymers of the prior art, are characterized in that the whole peptidic chain of the peptidic motifs is completely incorporated in the polymer and not pending from it. The process according to the invention allows thus to obtain a variety of motifs wherein alcane blocks and peptidic blocks are alternating thanks to the ratio of these two type blocks in the process.

The process of the invention involves aminopeptidic building blocks comprising at least two amino groups available for peptidic coupling (two primary or secondary amines, preferably two primary amines), which are reacted with a diacyl compound G, and optionally a diamine of formula $H_2N-Z-NH_2$. The process of the invention thus allows incorporating peptidic motifs within the nylon chain with different orientations (from the $C_{terminus}$ to the $N_{terminus}$ or from the $N_{terminus}$ to the $C_{terminus}$), thus leading to polymers with no symmetry in general.

Amino protecting groups are well known to a man skilled in the art. The amino protecting group is preferably suitable for peptide couplings, and for example can be selected in the group consisting of Fmoc, Boc, Cbz, Dde, trityl, NVoc, Alloc and Troc.

In an embodiment, the protected N-terminus of the AA or of the PEPTIDE (also noted PG(Nter)) can be protected by a protecting group selected in the group consisting of Fmoc, Boc, Cbz, Dde, trityl, NVoc, Alloc and Troc.

These groups are well known and regularly used in peptide synthesis where amino acid protection is needed to shield the various amino functional groups and N-terminus of a peptide. Orthogonal protection of amines may be needed in many cases as well in order to selectively protect and deprotect different groups on the same compound. This can be achieved through the use of Boc (base stable, acid labile) along with Fmoc (acid stable, base labile) amine protecting groups, a method frequently used in peptide synthesis. Methods for protection of amino groups with such above mentioned protecting groups are thus well known to a man skilled in the art and are well described in detail in the art and may be found in: Greene, "Protective Groups in Organic Synthesis", Wiley, New York, 2007 4th edition; Harrison et al. "Compendium of Synthetic Organic Methods", Vol. 1 to 8 (J. Wiley & sons, 1971 to 1996); Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol. E 22a, Vol. E 22b, Vol. E 22c, Vol. E 22d., M. Goodmann Ed., Georg Thieme Verlag, 2002.

The amino derivatization of the C-terminus group of amino-acid or peptide can be achieved by peptide chemistry techniques known to the man skilled in the art. The example of the present application describes one way of introducing ethylene diamine through SPPS techniques on trityl resin for example. Other methods for amino derivatization of the C-terminus may be applied.

The linear integration of the peptide in the polymer chain can be of interest when the extremities of the bioactive sequence of the peptide are not required for its activity or alternatively to modulate the degradability of the nylon by introducing substrates of endopeptidases (e.g. matrix metalo proteases, trypsin), triggering the degradation of the polymer chain placed in a dedicated environment.

Pendant peptide chains can also be easily introduced in the polymer backbone. Accordingly, the amino peptidic block comprises, within its peptidic chain or at any of its N terminus or C-terminus, a lysine or an amino acid residue having a side chain that contains the structure $-(CH_2)_m-NH_2$, wherein m is comprised between 0 and 10, preferably between 2 and 8.

According to this latter embodiment a "comb-type" configuration can be obtained structurally similar to what could be obtained by post-functionalization of a polyamide polymer chain. However, the process according to the present invention is much more attractive than post-functionalization approach as it enables an excellent control of the number of bioactive functions that are pending on the polymer chain. At last, it is also possible to combine several blocks in an appropriate ratio to yield multifunctional materials displaying several biological/physical properties.

The peptidic amino-building blocks used in the method according to the present invention comprise at least two free amino groups and up to three free amino groups able to engage in the polymerization.

The expression amino group according to the present invention able to engage in the polymerization corresponds to a primary or secondary amino group $R'''-NH_2$ or $R''R'''-NH$ wherein R" and R'" correspond to a $C_1$-$C_8$ alkyl group.

As explained above, the free amino group of the side chain of the AA or PEPTIDE may be the amino group of the side chain of a lysine residue or of a residue whose general formula is $-(CH_2)_m-NH_2$ wherein m is comprised between 0 and 10, preferably between 2 and 8.

Amino acids such as histidine, tryptophan or arginine contain a side chain with NH group but do not correspond to a reactive primary or secondary amino group according to the present invention in the sense that such NH groups are involved either in aromatic rings or in a guanidine in salt form and cannot engage in a polymerization reaction.

In the case the peptidic amino-building block comprises two free amino groups, the first can be the N-terminus of AA or of the PEPTIDE and the second can be the C-terminus amino derivatized and this case corresponds to the type A.

In another embodiment, the peptidic amino building block comprises three free amino groups, one being the N-terminus of the of AA, the second being the free amino group of the side chain of AA or of an amino-acid of the PEPTIDE and the third being the C-terminus amino derivatized and this case corresponds to the type B.

Yet in the embodiment where the peptidic amino building block comprises two free amino groups, the first can be the N-terminus of AA or of the PEPTIDE and the second can be the free amino group of the side chain of AA or of an amino-acid of the PEPTIDE and this case corresponds to the type C.

Yet in the embodiment where the peptidic amino building block comprises two free amino groups, the first can be the C-terminus amino derivatized and the second can be the free amino group of the side chain of AA or of an amino-acid of the PEPTIDE and this case corresponds to the type D.

Yet in the embodiment where the peptidic amino building block comprises two free amino groups, both can be the free amino group of the side chain of an amino-acid of the PEPTIDE and this case corresponds to the type E.

In the present description the expressions $(CH_2)_m$ or $(CH_2)_p$ or $(CH_2)_q$ are to be understood as comprising linear or ramified alkyl chains.

In the context of the present invention, the expression PEPTIDE corresponds to a natural peptide in the sense of a chain of amino acid residues bound by peptidic bonds, or a pseudopeptide or a modified peptide. As a matter of definition in the context of the present invention, the expression PEPTIDE thus corresponds to the homo- or hetero-oligomer according to the following motif:

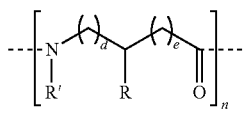

wherein:
- n is comprised between 2 and 25, particularly between 2 and 15, more particularly between 2 and 10, even more particularly between 2 and 5;
- R is the side chain of amino-acid that can be selected in the group consisting of natural amino acids side chains, non-natural amino acids side chains, modified or protected amino acids side chains;
- R' is H or an alkyl chain, linear or ramified, preferably methyl, ethyl, butyl, propyl, benzyl or a $C_3$-$C_6$ alkyl linked to R thus forming a R—R' ring;
- d and e being such that d+e=0 to 10.

Due to the nature of the PEPTIDE, several different peptidic amino building blocks belonging to a given type A, B, C, D or E may be used. Such building blocks may differ by the quantity and nature of the amino acids comprised in the peptide but they correspond to the general formula A, B, C, D or E in the sense that they exhibit two or three free primary or secondary amino groups available to engage in the polymerization.

Accordingly, different type A building blocks can be used that differ in the nature and/or quantity of amino acid residues of the polypeptidic chain.

Accordingly, different type B building blocks can be used that differ in the nature and/or quantity of amino acid residues of the polypeptidic chain.

Accordingly, different type C building blocks can be used that differ in the nature and/or quantity of amino acid residues of the polypeptidic chain.

Accordingly, different type D building blocks can be used that differ in the nature and/or quantity of amino acid residues of the polypeptidic chain.

Accordingly, different type E building blocks can be used that differ in the nature and/or quantity of amino acid residues of the polypeptidic chain.

The PEPTIDE of the amino-building block can be any type of peptide but is preferably a bioactive peptide.

Preferred sequences of PEPTIDE can be selected in the group consisting of Gly-Phe-Arg, Lys-Gly-Phe-Arg, Arg-Arg and Lys-Ahx-Arg-Arg.

In a further embodiment of the present invention, the amino-building block can be labelled with a probe, such as a fluorophore. Accordingly, in a first embodiment, a free amino group of the side chain of AA or of an amino-acid residue of PEPTIDE can be modified with a probe.

The probe may be chosen in the group consisting of fluorescein, fluorescein salt, 4',5'-Bis[N,N-bis(carboxymethyl)-aminomethyl]fluorescein, 6-[fluoresceine-5(6)-carboxamido]hexanoic acid, 6-[fluoresceine-5(6)-carboxamido]hexanoic acid, N-hydroxysuccinimide fluorescein-5(6)-isothiocyanate ester, fluorescein-α-D-N-acetylneuraminide-polyacryl-amide, fluorescein amidite, fluorescein-di(β-D-galactopyranoside), fluorescein-di-(β-D-glucopyranoside), fluorescein diacetate, fluorescein-5(6)-isothiocyanate diacetate, fluorescein-5-maleimide diacetate, fluorescein-6-isothiocyanate diacetate, fluorescein dibutyrate, fluorescein dilaurate, fluorescein-hyaluronic acid, isothiocyanate de fluorescein, fluorescein-dextran isothiocyanate, mercury-fluorescein acetate, mono-p-guanidinobenzoate-fluorescein chlorhydrate, fluorescein O,O'-diacrylate, fluorescein O,O'-dimethacrylate, fluorescein o-acrylate, fluorescein O-methacrylate, fluorescein N-hydroxysuccinimide ester, fluorescein-5-thiosemicarbazide, fluorescein-α-D-galactosamine polyacrylamide, fluorescein-α-D-mannopyranoside-polyacrylamide, 4(5)-(iodoacetamido)-fluorescein, 5-(Bromomethyl)fluorescein, 5-(Iodoacetamido)fluorescein, aminophenyl-fluorescein, Biotin-4-fluorescein, hydroxyphenyl-fluorescein, MTS-4-fluorescein, poly(fluorescein-O-acrylate), poly(fluorescein-O-methacrylate), PPHT-fluorescein acetate, 5(6)-(Biotinamidohexanoylamido)pentylthioureidylfluorescein, N-(5-fluoresceinyl)maleimide, fluorescein-di-[methylene-N-methylglycine], erythrosin B, ethyl eosin, 5-carboxy fluorescein, ester N-succinimidyl de 5-carboxy fluorescein, 6-Carboxy-fluoresceinN-hydroxysuccinimide ester, dibenzyl fluorescein, rhodol, 6-amino fluorescein, rhodamine 6G, rhodamine B and rhodamine 123.

Methods for grafting probe on a peptide, particularly on the amino group of the side chain of an amino acid, are well known to the skilled person and easily available.

In another embodiment, the probe can be grafted on the N-terminus of the AA or of the PEPTIDE, which in this case contains a side chain with a free amino group to engage in the polymerization and a C-terminus amino derivatized as explained above.

The present invention further relates to a bioorganic nylon type polymer obtainable according to the process of the invention.

The bioorganic nylon type polymer of the invention comprises or consists of at least one group of repeated unit, said group being selected from:

a) group a consisting of repeated units of formula A1 and A2

(A1)

and.

(A2)

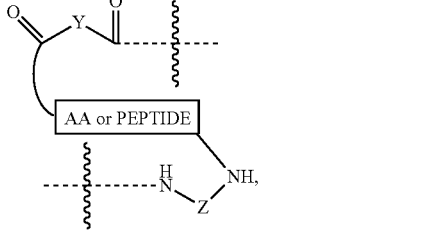

and/or
b) group b consisting of repeated units of formula B1 to B8:
and/or
c) group c consisting of repeated units of formula C1 and C2:
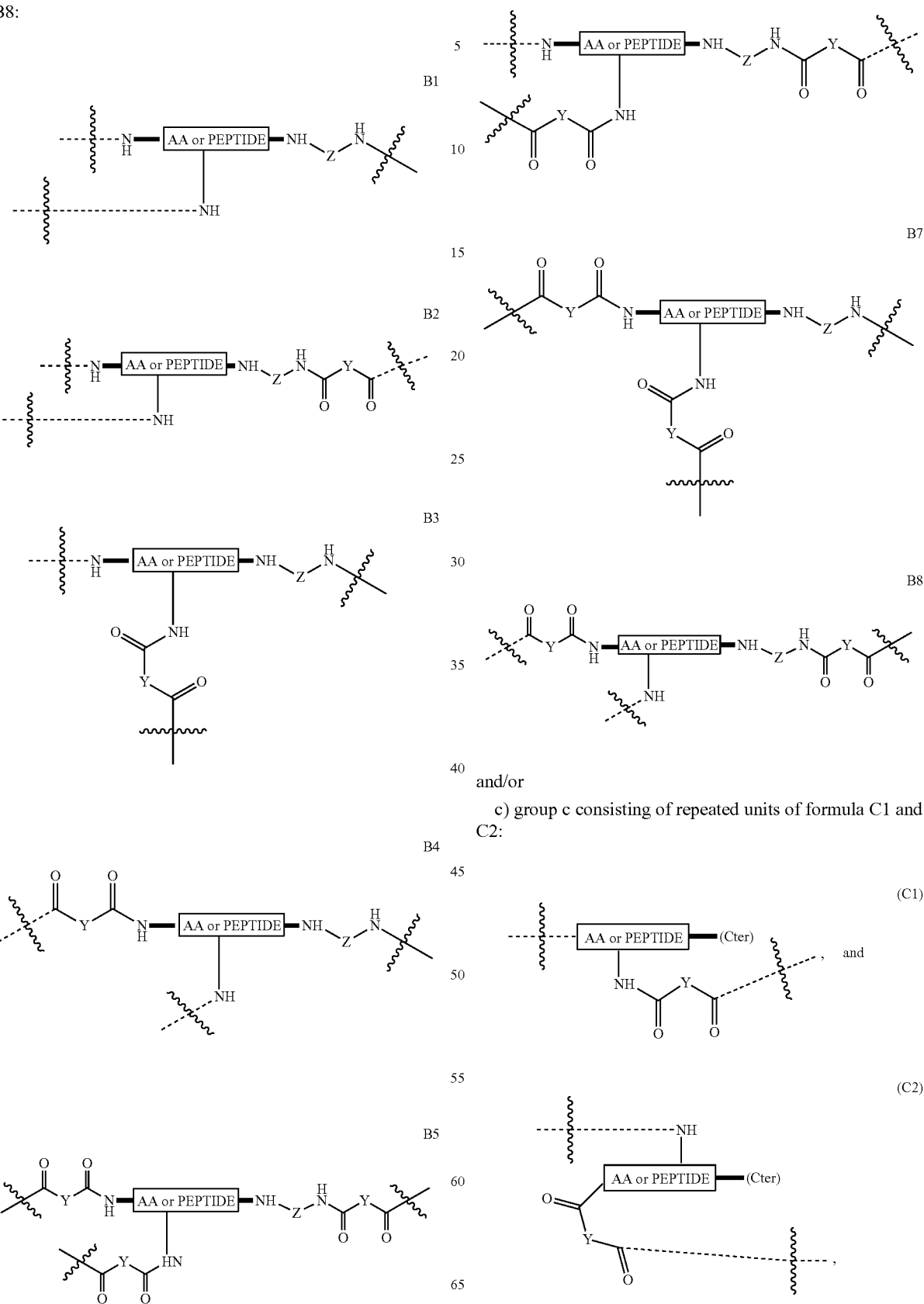

and/or
d) group d consisting of repeated units of formula D1 and D2:

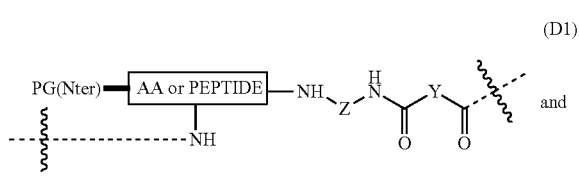
(D1)

and

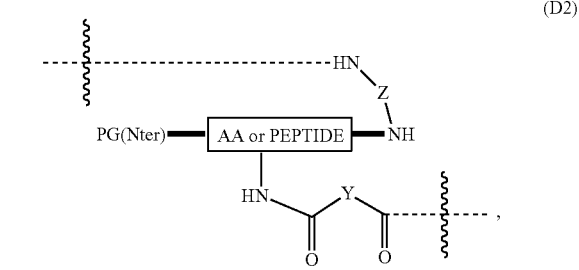
(D2)

and/or
e) group e consisting of repeated units of formula E1 and E2:

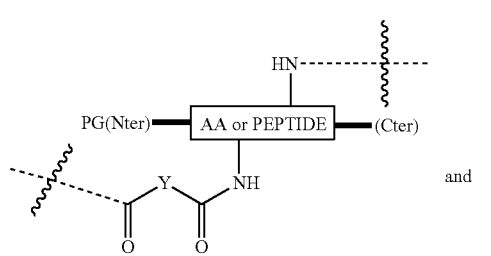
(E1)

and

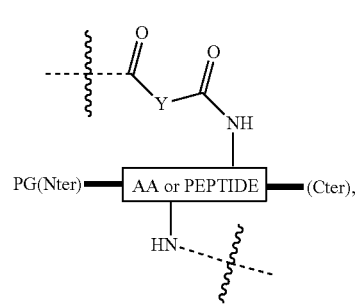
(E2), wherein each AA, PEPTIDE, PG(Nter), Y and Z are independently as defined above, and (Cter) denotes the $C_{terminus}$ of AA or PEPTIDE.

As used herein, the $C_{terminus}$ of AA or PEPTIDE is understood as derivatized or not derivatized.

In one embodiment, it is not derivatized, the $C_{terminus}$ is then a free carboxylic acid COOH.

In another embodiment, it is derivatized. Examples of derivatized $C_{terminus}$ are $CONH_2$, COOR, CONHR, CON-$R_aR_b$ with $R_a$ and $R_b$ independently representing a linear or ramified ($C_1$-$C_6$, preferably $C_1$-$C_4$) alkyl, aryl or aralkyl.

As used herein, an "alkyl" refers to a straight or branched monovalent saturated hydrocarbon chain, preferably containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "aryl", as used in the present invention, refers to an aromatic group comprising preferably 5 to 10 carbon atoms and comprising one or more fused rings, such as, for example, a phenyl or naphthyl group. Advantageously, it will be a phenyl group. Optionally, the aryl is substituted, by one or more substituents for instance selected from alkyl, OH, Oalkyl, $NH_2$, NHalkyl, N(alkyl)$_2$.

The term "aralkyl" or "aryl-($C_1$-$C_6$)alkyl", as used in the present invention, refers to an aryl group as defined above bound to the molecule via an alkyl group as defined above. In particular, an aralkyl group is a benzyl group.

The dashed bonds

are bonds connecting one repeated unit to another.

Of note, following usual conventions in the field of peptides, the above repeated units are oriented from the N-terminus (left side of the unit) to the C-terminus (right side of the unit). Also, as explained above in connection with the monomers B, C, D and E, repeated units B1-B8, C1, C2, D1, D2, E1 and E2 comprise an aminoacid or peptide with at least one (one for C1, C2, 2 for D1, D2, E1 and E2, and 3 for B1-B8) pending amino group as linking part between two repeated units.

Depending on whether block B has been used in the process of the invention, the bioorganic nylon type polymer may be linear or crosslinked.

In a first embodiment, the bioorganic nylon type polymer is linear. As each aminopeptidic monomer contains at least two free amino groups that can be engaged in the polymerization reaction with the diacyl group, the bioorganic nylon type polymer has no symmetry. In other words, the bioorganic nylon type polymer of the invention is not an alternating copolymer, but may rather be defined as a random copolymer.

In this first embodiment, the bioorganic nylon type polymer comprises or consists of groups of repeated unit selected from groups a, c, d, and/or e as defined above.

In a particular variant of this first embodiment, the bioorganic nylon type polymer comprises 2 groups of repeated units selected from group a, group c, group d and group e. In another variant, the bioorganic nylon type polymer comprises 3 groups of repeated units selected from group a, group c, group d and group e. In another variant, the bioorganic nylon type polymer comprises all 4 groups of repeated units a, c, d and e.

In a particular variant, the bioorganic nylon type polymer is obtained by using only amino-building blocks A. The bioorganic nylon type polymer then consists of repeated units (A1) and (A2). In this variant, the bioorganic nylon type polymer is of formula:

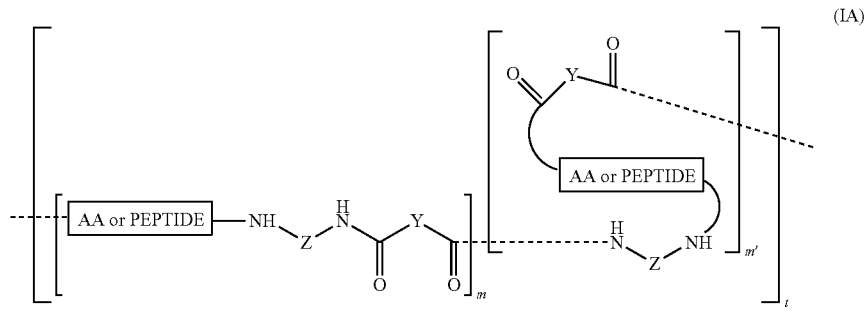

(IA)

wherein each AA, PEPTIDE, Y and Z are independently as defined above, and m and m' are independently selected from positive real numbers, for instance integers selected from 0 and 2000, for instance between 1 and 1000, m and m' may not be simultaneously 0, and t is a positive integer preferably from 1 to 2000 or between 1 and 1000.

For instance, the bioorganic nylon type polymer is of formula

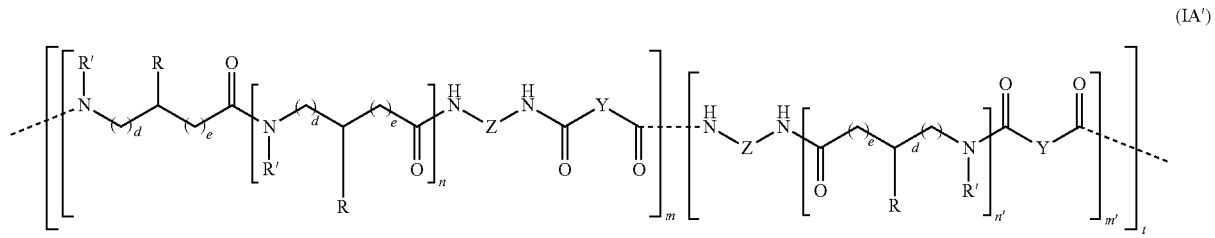

(IA')

wherein each R, R', Y, Z, d and e are independently as defined above, n is a positive real numbers, for instance an integer, which may not be 0, preferably between 2 and 1000, and m and m' are independently selected from positive real numbers, for instance integers selected from 0 and 2000, for instance between 1 and 1000, m and m' may not be simultaneously 0, and t is a positive integer preferably from 1 to 2000 or between 1 and 1000.

In a particular variant, the bioorganic nylon type polymer is obtained by using only amino-building blocks C. The bioorganic nylon type polymer then consists of repeated units (C1) and (C2). In this variant, the bioorganic nylon type polymer is of formula:

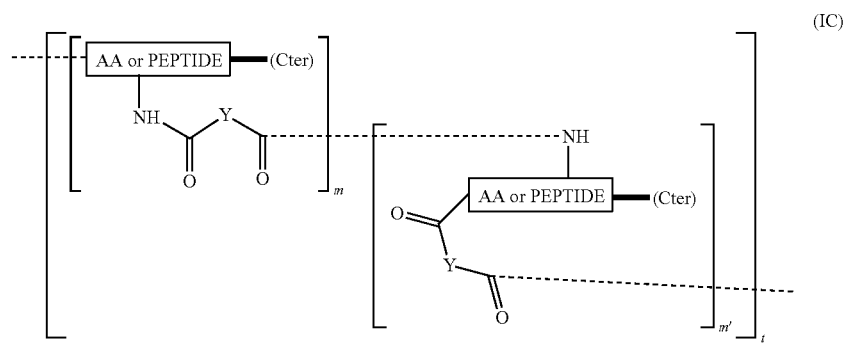

(IC)

wherein each AA, PEPTIDE, (Cter), Y and Z are independently as defined above, and m and m' are independently selected from positive real numbers, for instance integers selected from 0 and 2000, for instance between 1 and 1000, m and m' may not be simultaneously 0, and t is a positive integer preferably from 1 to 2000 or between 1 and 1000.

For instance, the bioorganic nylon type polymer is of formula

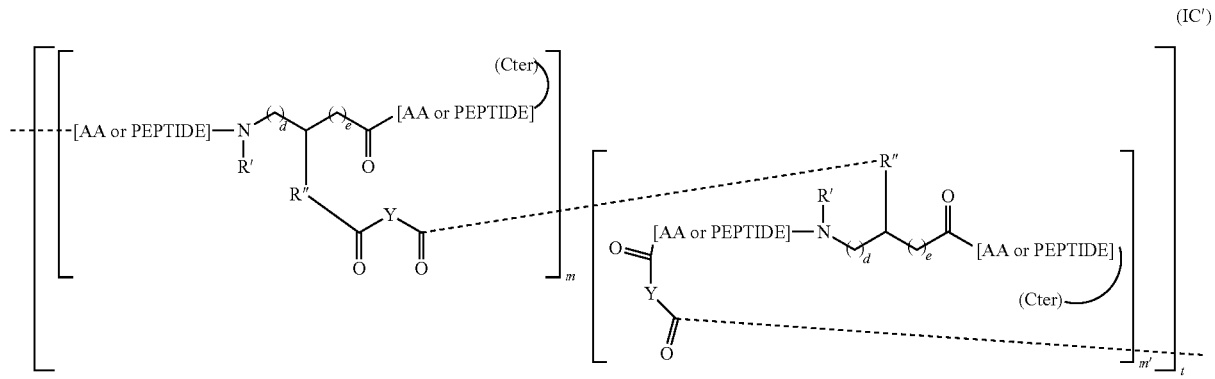

(IC')

wherein each AA, PEPTIDE, PG(Cter), R', R", Y, Z, d and e are independently as defined above, m and m' are independently selected from positive real numbers, for instance integers selected from 0 and 2000, for instance between 1 and 1000, m and m' may not be simultaneously 0, and t is a positive integer preferably from 1 to 2000 or between 1 and 1000.

In a particular variant, the bioorganic nylon type polymer is obtained by using only amino-building blocks D. The bioorganic nylon type polymer then consists of repeated units (D1) and (D2). In this variant, the bioorganic nylon type polymer is of formula:

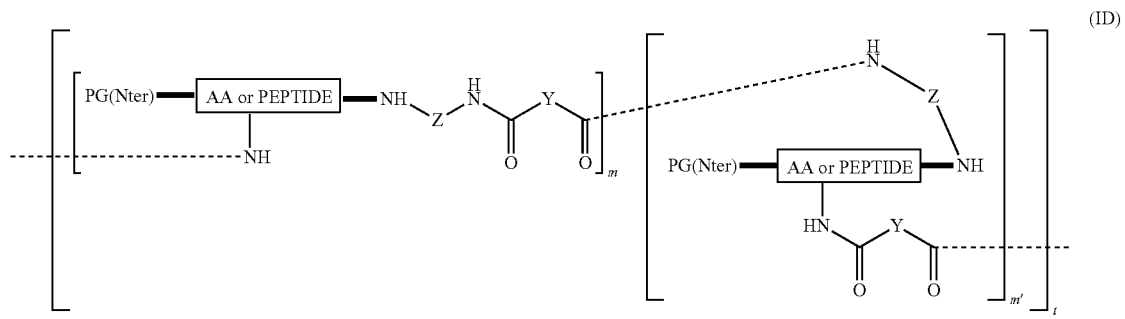

(ID)

wherein each AA, PEPTIDE, PG(Nter), Y and Z are independently as defined above m and m' are independently selected from positive real numbers, for instance integers selected from 0 and 2000, for instance between 1 and 1000, m and m' may not be simultaneously 0, and t is a positive integer preferably from 1 to 2000 or between 1 and 1000.

For instance, the bioorganic nylon type polymer is of formula

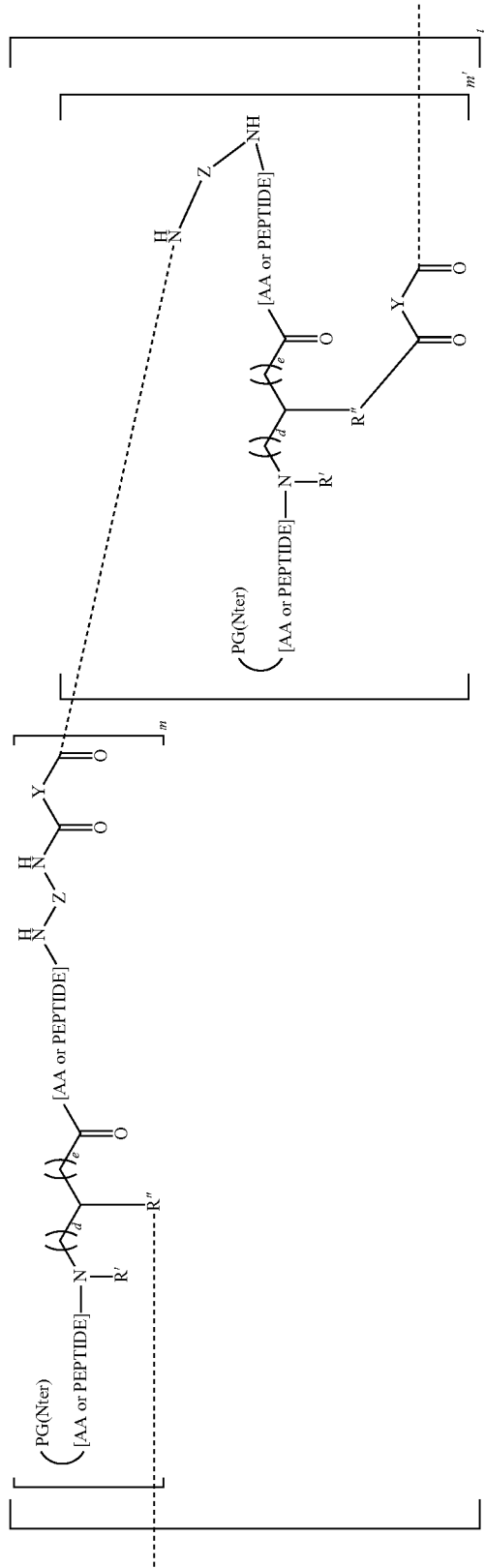

wherein each AA, PEPTIDE, PG(Nter), R', R", Y, Z, d and e are independently as defined above, m and m' are independently selected from positive real numbers, for instance integers selected from 0 and 2000, for instance between 1 and 1000, m and m' may not be simultaneously 0, and t is a positive integer preferably from 1 to 2000 or between 1 and 1000.

In a particular variant, the bioorganic nylon type polymer is obtained by using only amino-building blocks E. The bioorganic nylon type polymer then consists of repeated units (E1) and (E2). In this variant, the bioorganic nylon type polymer is of formula:

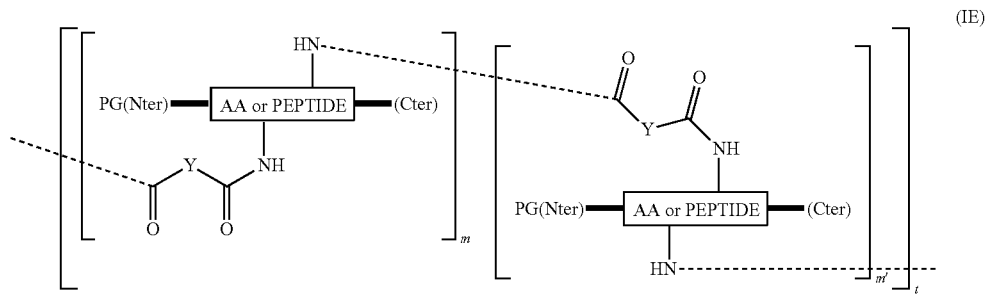

wherein each AA, PEPTIDE, PG(Nter), (Cter), Y and Z are independently as defined above m and m' are independently selected from positive real numbers, for instance integers selected from 0 and 2000, for instance between 1 and 1000, m and m' may not be simultaneously 0, and t is a positive integer preferably from 1 to 2000 or between 1 and 1000.

For instance, the bioorganic nylon type polymer is of formula

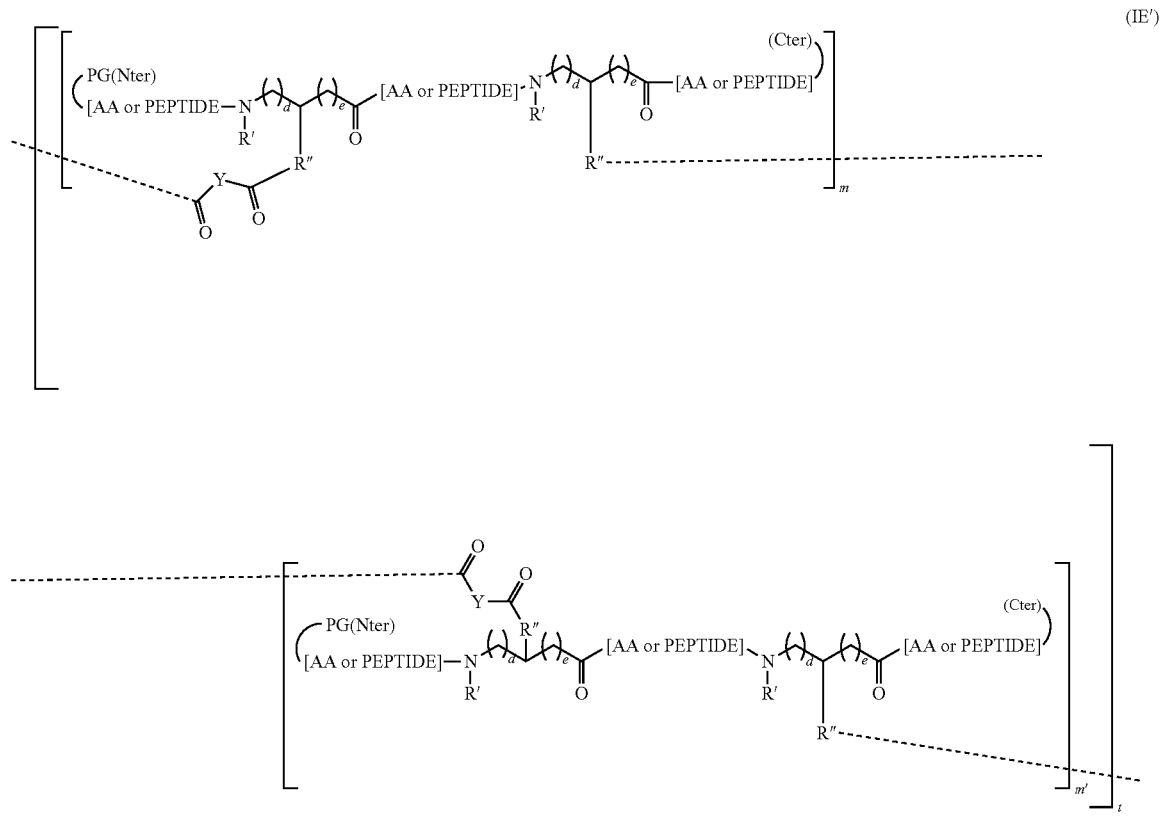

wherein each AA, PEPTIDE, PG(Nter), (Cter), R', R", Y, Z, d and e are independently as defined above, m and m' are independently selected from positive real numbers, for instance integers selected from 0 and 2000, for instance between 1 and 1000, m and m' may not be simultaneously 0, and t is a positive integer preferably from 1 to 2000 or between 1 and 1000.

In a second embodiment, the bioorganic nylon type polymer is cross-linked.

It thus contains at least repeated units B1 to B8 (i.e. group b of repeated units) as defined above.

In a particular variant, the cross-linked bioorganic nylon type polymer further comprises repeated units A1 and A2.

In a particular variant, the cross-linked bioorganic nylon type polymer further comprises repeated units $C_1$ and $C_2$.

In a particular variant, the cross-linked bioorganic nylon type polymer further comprises repeated units D1 and D2.

In a particular variant, the cross-linked bioorganic nylon type polymer further comprises repeated units E1 and E2.

In a particular variant, the cross-linked bioorganic nylon type polymer further comprises any 2 groups of repeated units selected from group a, group c, group d and group e.

In a particular variant, the cross-linked bioorganic nylon type polymer further comprises any 3 groups of repeated units selected from group a, group c, group d and group e.

In a particular variant, the cross-linked bioorganic nylon type polymer further comprises repeated units A1, A2, $C_1$, $C_2$, D1, D2, E1 and E2. In particular, it consists of repeated units A1, A2, B1 to B8, $C_1$, $C_2$, D1, D2, E1 and E2.

Such bioorganic nylon type polymer (be it linear or cross-linked) can be characterized by differential scanning calorimetry, elemental analysis, steric exclusion chromatography, amino acid analysis for example.

The present invention also relates to the use of the bioorganic nylon type polymer obtained according to the present process for the manufacture of material, particularly biomaterial, more particularly antibacterial material.

In one embodiment, the material is resorbable, particularly bioresorbable.

In one embodiment, the present invention concerns the use of bioorganic nylon type polymer according to the present invention for the manufacture of material, particularly an antibacterial material, more particularly a biomaterial, even more particularly a bioresorbable material It is also an object of the present invention to provide material comprising, or consisting of a bioorganic nylon type polymer according to the present invention.

Such material can be selected in the group consisting of antibacterial material, anti-inflammatory material, biocide material, fungicide materials.

It is also an object of the present invention to provide medical device or a fabric comprising a bioorganic nylon type polymer according to the present invention. Advantageously, the bioorganic nylon type polymer provides the medical device or fabric with antibacterial, anti-inflammatory, biocide and/or fungicide properties.

The medical device may be a filter for body fluids or a suture or a catheter or a dressing or an implantable device for example.

The fabric can be a sock, a shoe sole, stockings, or a shirt for example.

A further object of the present invention lies in the use of the bioorganic nylon type material according to the present invention for the manufacture of sensor material, particularly material that reacts to environmental modification.

Indeed, the presence of peptides, particularly bioactive peptides embedded in the bioorganic nylon type polymer of the invention, allows having a material that reacts to any modification of the environment and that can be used as biosensor.

EXAMPLES

Figure 1:
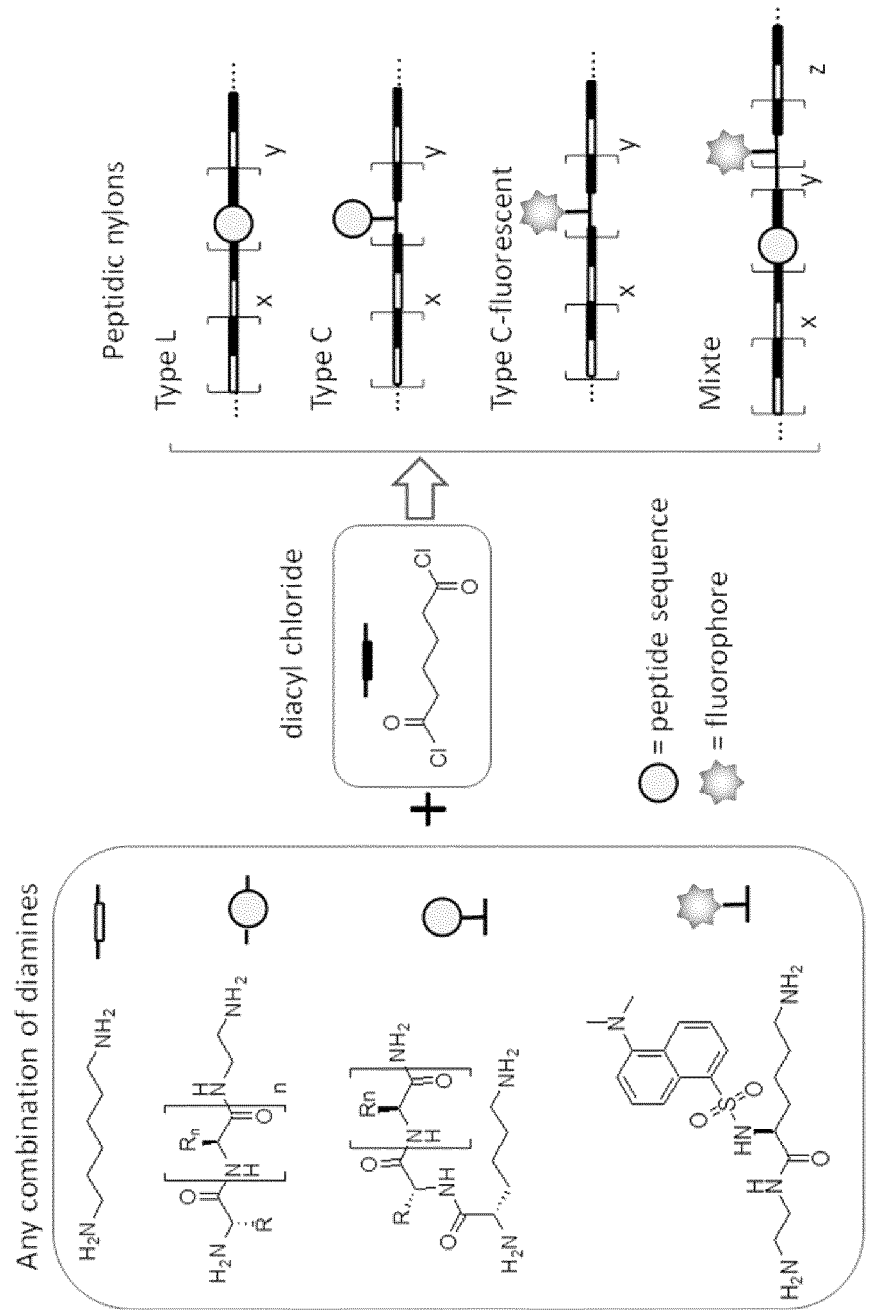
FIG. 1 depicts the general procedure for the preparation of bioorganic nylon type polymer according to the present invention.
Figure 2:
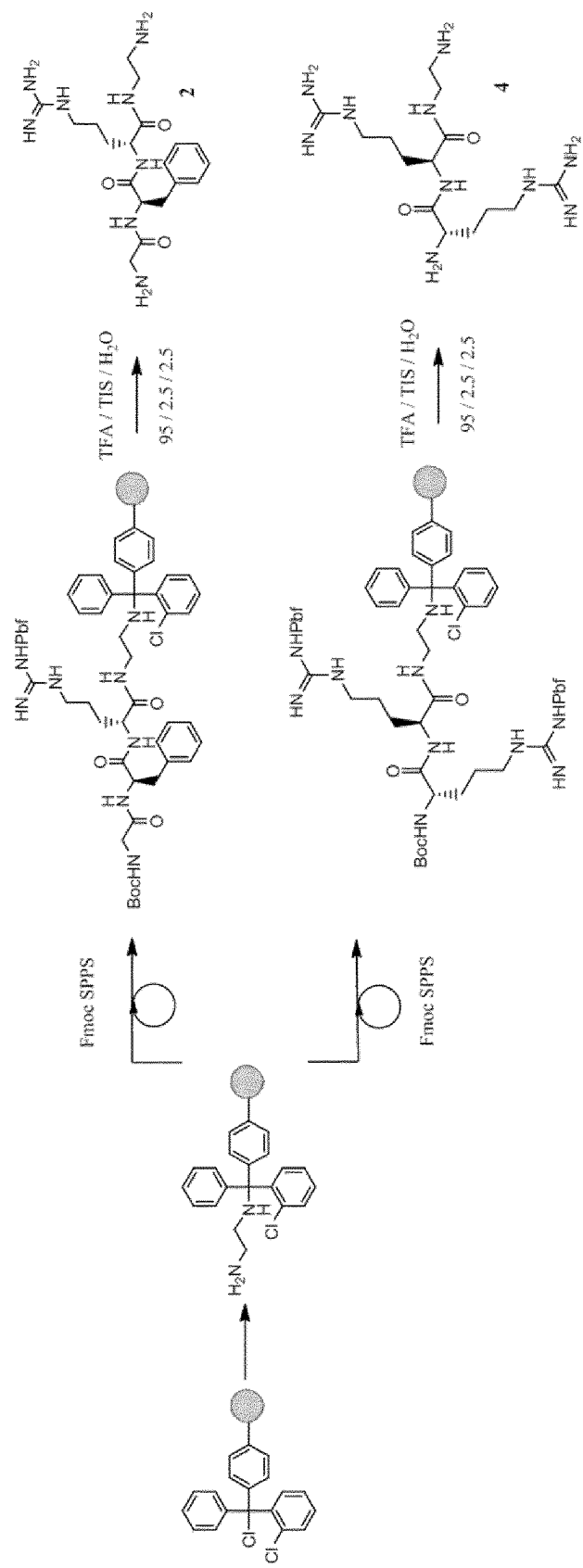
FIG. 2 depicts the general procedure of synthesis route for the preparation of amino peptide building blocks 2 and 4 of Table 1.
Figure 3:
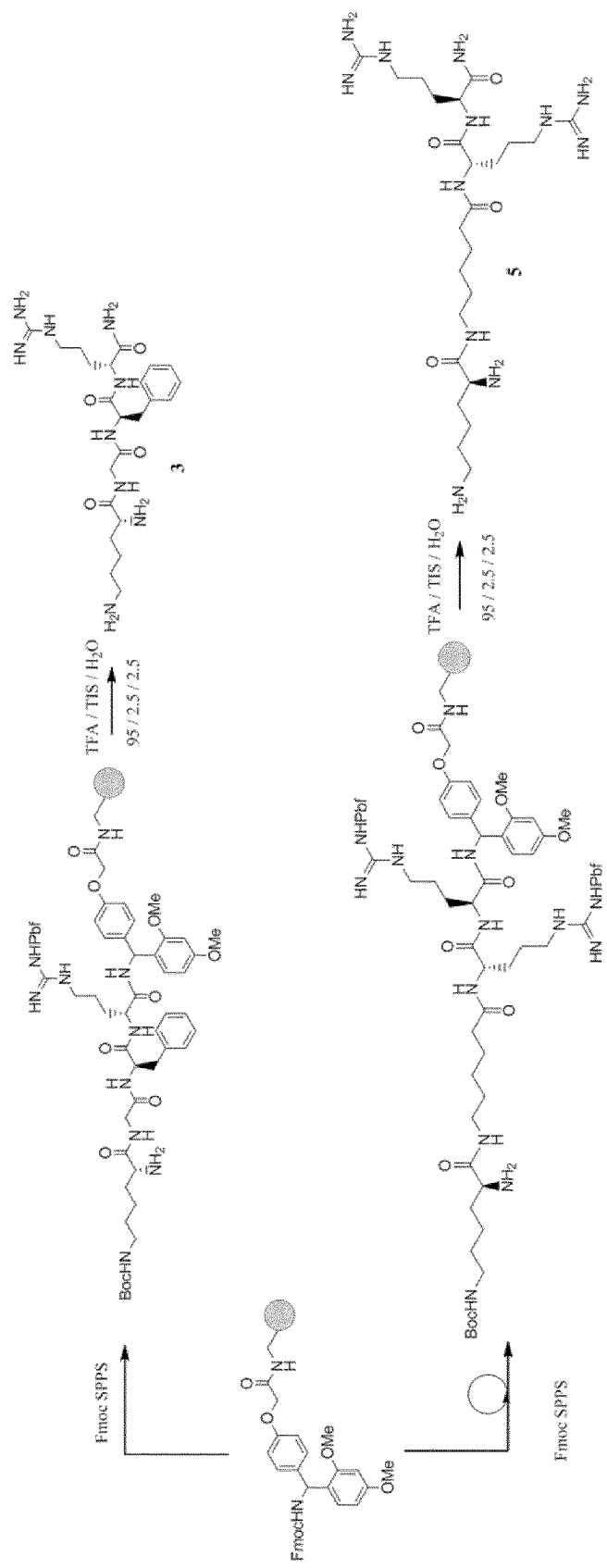
FIG. 3 depicts the general procedure of synthesis route for the preparation of amino peptide building blocks 3 and 5 of Table 1.

Example 1: Preparation of a Nylons N1 with Amino Building Block Compound 1 DanLysNHCH$_2$CH$_2$NH$_2$ Compound 1 was prepared by Fmoc SPPS using trityl chloride resin which was first reacted with ethylene diamine.

The introduction of a ethyle diamine of formula H$_2$N—(CH$_2$)$_2$—NH$_2$ on 2-chlorotrityl is described in numerous paper and, as an example in 'A New Way to Silicone Based Peptide Polymers', Said Jebors, Jeremie Ciccione, Soultan Al-Halifa, Benjamin Nottelet, Christine Enjalbal, Celine M'Kadmi, Muriel Amblard, Ahmad Mehdi, Jean Martinez and Gilles Subra. *Angew. Chem. Int. Ed.*, Volume 54, Issue 12, pages 3778-3782, Mar. 16, 2015.

In this case, the introduction of diamine on chloride resin was achieved as follows: To a pre-swollen suspension of 2-chlorotrityl chloride resin (1.44 mmol Cl/g, 5 g) in CH$_2$Cl$_2$, was added a solution of ethylene diamine (1.44 ml, 3 equiv.), DIEA (8.8 ml, 7 equiv.) in DMF (50 ml). The reaction mixture was agitated at room temperature overnight, then washed with DMF (3×), DCM (3×), MeOH (1×) and DCM (1×).

After coupling of FmocLys(Boc)OH on the primary amine group, Compound 1 was obtained according to the following scheme and used without further purification.

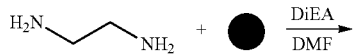

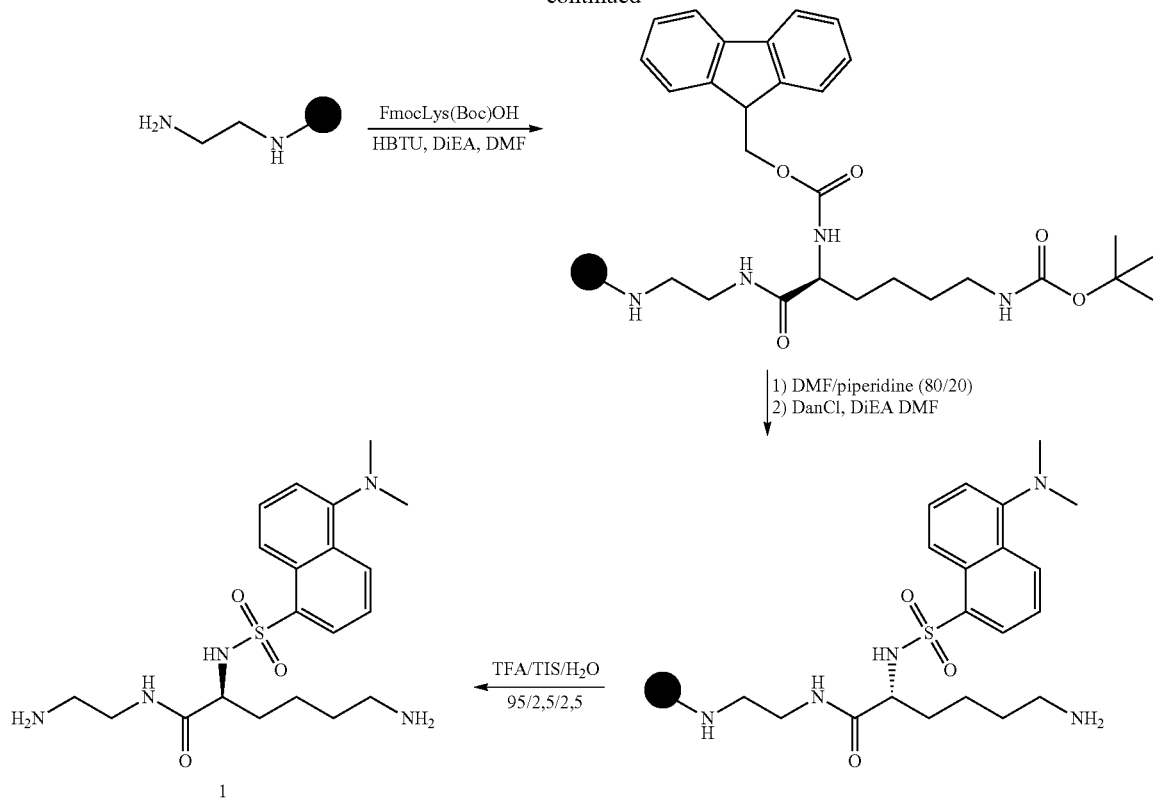

Fluorescent nylons N1 were prepared first by solubilizing adipoyl dichloride in DCM (0.4 M). Then a thin layer of 0.5 M NaOH solution was deposited with a pipette over the organic phase. Finally, a mixture of 1 and 1,6 diamino hexane (10/100, 1/100 and 0.1/100; total concentration=0.4 M) in 0.5 M NaOH was slowly deposited over the organic phase.

Polymerization happens immediately at the interface. The resulting polymer is pulled out manually with a stick from the beaker. White and resistant wire of over one meter long can be obtained with variable thickness, depending on its length. After washing in various solvents to eliminate unreacted species and drying under vacuum, the wire appears to be harsher and resistant but not so much elastic even though it remains flexible. The yield was nearly quantitative (>99%) implying that the peptide was probably fully consumed as diamine building block in the polymer.

Example 2: Preparation of Various Nylon

Similarly and using the described experimental procedure as in example 1, four other peptide sequences (2-5 in Table 1) were synthesized either on Rink amide-PS (type C), or on 2-Chloro-Chloro-Trityl-PS resin first functionalized with Fmoc ethylene diamine (type L).

After cleavage from the resin, the peptides were purified by preparative RP-HPLC. Compounds 2 and 3 shared the same Gly-Phe-Arg peptide sequence, incorporated in the polymer backbone in a linear way (type L) or as pendant chains (type C) through a N-terminus lysine. Peptides 4 and 5 are cationic sequences derived from the short antibacterial amphipathic Palm-Arg-Arg-NH2 peptide designed in our laboratory. Interestingly, derivatives of such peptide were grafted on a glass surface or incorporated in new bioorganic polymers including peptide-silicone. The resulting hybrid materials kept antibacterial properties against $E.\ Coli$, consolidating the fact that the mode of action of this antibacterial peptide involves the destabilization of the bacterial membrane. Peptide 5 leads to a nylon containing the antibacterial peptide sequence in a comb configuration, while peptide 4 lead to a linear nylon containing the antibacterial peptide sequence. The same procedure used for N1 was applied to the synthesis of other peptide nylons. Peptides 2-5 were used in different x/y ratios with 1,6-diamino hexane yielding twelve different nylons (Table 1). In addition, a fluorescent nylon N6, incorporating the dansyl derivative 1 (1%) and the peptide 4 (9%) was prepared.

All nylons, including N0 not containing any peptide sequence, were characterized by ATG and DSC to determine glass transition temperature, fusion and solidification temperature. The profiles were comparable with conventional 1-6 nylons indicating that introduction of 1-10% peptide related to conventional 1.6-diamino, does not really affect the mechanical properties.

TABLE 1

Peptide Nylons

| Peptide | Type[a] | Peptide sequence | Peptide nylon | x/y ratio[b] |
|---|---|---|---|---|
| | | Std nylon 6.6 prepared with diaminohexane | N0 | 0/100 |
| 1 | | DanLysNHCH$_2$CH$_2$NH$_2$ | N1-10% | 1/10 |
| | | " | N1-1% | 1/100 |
| | | " | N1-0.1% | 1/1000 |

TABLE 1-continued

Peptide Nylons

| Peptide | Type[a] | Peptide sequence | Peptide nylon | x/y ratio[b] |
|---|---|---|---|---|
| 2 | L | HGlyPheArgNHCH$_2$CH$_2$NH$_2$ | N2-10% | 1/10 |
|  | L | " | N2-1% | 1/100 |
|  | L | " | N2-0.1% | 1/1000 |
| 3 | C | HLysGlyPheArgNH$_2$ | N3-10% | 1/10 |
|  | C | " | N3-1% | 1/100 |
|  | C | " | N3-0.1% | 1/1000 |
| 4 | L | HArgArgNHCH$_2$CH$_2$NH$_2$ | N4-10% | 1/10 |
|  | L | " | N4-1% | 1/100 |
|  | L | " | N4-0.1% | 1/1000 |
| 5 | C | HLysAhxArgArgNH$_2$ | N5-10% | 1/10 |
|  | C | " | N5-1% | 1/100 |
|  | C | " | N5-0.1% | 1/1000 |
| 4 and 1 | M | HArgArgNHCH$_2$CH$_2$NH$_2$ DanLysNHCH$_2$CH$_2$NH$_2$ | N6-10% | 9/1/100[c] |

[a] see FIG. 1: L means linear peptide-nylon, C means comb-like peptide-nylon, M means multifunctional peptide nylon
[b] x/y molar ratio of peptide/diamino hexane
[c] x/y/z molar ratio of peptide 4/diamino hexane/compound 1

Example 3: Procedure for the Synthesis of Peptide-Nylon N2-1%

Firstly, a 0.4 M solution of adipoyl chloride (625 µL) in dichloromethane (10.7 ml) was introduced in a 20 mL beaker.

Then a solution of 0.4M of a mixture of 1.6 diamino hexane (449 mg) and peptide sequence 3 (221 mg) in 10.7 mL of 0.5 M NaOH is gently deposited with a pipette on the top of the organic solution of adipoyl chloride.

Polymerization happens immediately at the interface. The resulting polymer is pulled out manually with a stick from the beaker and washed with 10 mL of methanol (3×), 10 mL of water (3×), 10 mL of acetone (3×) and dried.

Example 4: Procedure for the Synthesis of Peptide-Nylon N2-100%

Firstly, a 0.4 M solution of adipoyl chloride (312.5 µL) in dichloromethane (5.3 ml) was introduced in a 20 mL beaker.

Then a solution of 0.4M of a peptide sequence 2 (1.4 g) in 5.3 mL of 0.5 M NaOH is gently deposited with a pipette on the top of the organic solution of adipoyl chloride.

Polymerization happens immediately at the interface. The resulting polymer is pulled out manually with a stick from the beaker and washed with 10 mL of methanol (3×), 10 mL of water (3×), 10 mL of acetone (3×) and dried.

Example 5 Procedure for the Synthesis of Peptide-Nylon N2-100%

To a 0.1 M solution of peptide sequence 2 (0.35 g) in DMF was added DIEA (6 eq., 684 µL) and adipoyl chloride (1 eq., 78.1 µL). The reaction mixture was allowed to stir until precipitation of the polymer. The resulting polymer is filtered and washed with 10 mL of methanol (3×), 10 mL of water (3×), 10 mL of acetone (3×) and dried.

Example 6 Procedure for the Synthesis of Peptide-Nylon N3-1%

Firstly, a 0.4 M solution of adipoyl chloride (625 µL) in dichloromethane (6.15 ml) was introduced in a 20 mL beaker.

Then a solution of 0.4M of a mixture of 1.6 diamino hexane (449 mg) and peptide sequence 3 (221 mg) in 6.15 mL of 0.5 M NaOH is gently deposited with a pipette on the top of the organic solution of adipoyl chloride.

Polymerization happens immediately at the interface. The resulting polymer is pulled out manually with a stick from the beaker and washed with 10 mL of methanol (3×), 10 mL of water (3×), 10 mL of acetone (3×) and dried.

The invention claimed is:
1. A process for preparation of bioorganic nylon type polymers comprising the steps of
i) preparing a basic solution containing a peptidic amino-building block DanLysNHCH$_2$CH$_2$NH$_2$ of the following formula:

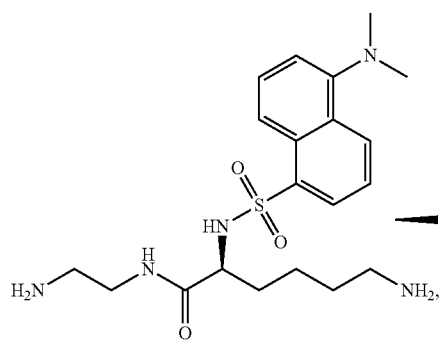

and
a diamino building block F selected from the group consisting of diamino-alkane building block of general formula (F): H$_2$N—Z—NH$_2$,
wherein:
Z is (CH$_2$)$_p$; and
p is between 1 and 14,
ii) Initiating polymerization by contacting the solution of i) with a solution containing a diacyl G of the following formula (G): X(CO)—Y—(CO)X
wherein:
X is a halogen;
Y is (CH$_2$)$_q$;
q is between 1 and 12.
2. The process of claim 1, wherein the diamino building block F is diamino hexane.
3. The process of claim 1, wherein the diacyl G is adipoyl chloride.
4. The process of claim 1, wherein:
Z is (CH$_2$)$_p$, C$_6$H$_4$, C$_6$H$_4$—W'—C$_6$H$_4$, C$_6$F$_4$, C$_6$F$_4$—W'—C$_6$F$_4$, or C$_{10}$H$_6$;
W' is a bond, CH$_2$, O, S, or Si$_2$(CH$_2$)$_5$CH$_3$]$_2$ with s comprised between 1 and 4.
5. The process of claim 1, wherein the polymerization is achieved in homogeneous or heterogeneous phase.
6. The process of claim 1, wherein the polymerization is achieved in homogeneous phase and the peptidic amino-buildings block is dissolved in a solvent, which is also a solvent of the diacyl compound G.
7. The process of claim 1, wherein the polymerization is achieved in heterogeneous phase and polymerization is initiated through interfacial polymerization.
8. The process of claim 1, wherein the polymer is recovered and washed.
9. The process of claim 1, wherein the basic solution of i) has a pH above 7.
10. The process of claim 1, wherein the diacyl compound (G) is diacyl chloride.
11. The process of claim 1, wherein the molar concentration of the peptidic-diamino building block varies from 1 to 100% and the molar concentration of diamino-alkane building block (F) is between 0 and 99%, the sum of both molar quantities being equal to 100% and corresponding to the molar quantity of diacyl compound (G) expressed as 100%.
12. The process of claim 1, wherein a N-terminus of the peptidic amino-building block is protected by a protecting group selected from the group consisting of Fmoc, Boc, Cbz, Dde, trityl, NVoc, Alloc and Troc.
13. The process of claim 1, wherein the peptidic amino-building block comprises, within a peptidic chain or at an N terminus or C-terminus, a lysine or an amino acid residue having a side chain that contains the following structure:
—(CH$_2$)$_m$—NH$_2$ wherein m is between 0 and 10.
14. The process of claim 1, wherein the peptidic amino-building block corresponds to a homo-or hetero-oligomer according to the following motif:

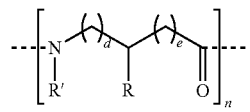

wherein:
n is comprised between 2 and 25;
R is the side chain of an amino-acid selected from the group consisting of natural aminoacids side chains, non-natural aminoacids side chains, and modified aminoacids side chains;
R' is H or a C3-C6 alkyl linked to R thus forming a R—R' ring; and d and e being such that d+e=0 to 10.
15. The process of claim 1, wherein the peptidic amino-building block is labelled with a probe.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: artificial
<220> FEATURE:
<223> OTHER INFORMATION: Peptide nylons
<220> FEATURE:
<221> NAME/KEY: MOD_RES
<222> LOCATION: (4)..(4)
<223> OTHER INFORMATION: AMIDATION

<400> SEQUENCE: 1

Lys Gly Phe Arg
1

<210> SEQ ID NO 2
<211> LENGTH: 4
<212> TYPE: PRT
<213> ORGANISM: artificial
<220> FEATURE:
<223> OTHER INFORMATION: Peptide nylons
<220> FEATURE:
<221> NAME/KEY: MOD_RES
<222> LOCATION: (2)..(2)
<223> OTHER INFORMATION: Xaa is Ahx
<220> FEATURE:
<221> NAME/KEY: MOD_RES
```

```
<222> LOCATION: (4)..(4)
<223> OTHER INFORMATION: AMIDATION

<400> SEQUENCE: 2

Lys Xaa Arg Arg
1
```